(12) United States Patent
Sturlesi et al.

(10) Patent No.: US 11,998,654 B2
(45) Date of Patent: Jun. 4, 2024

(54) SECURING IMPLANTS AND MEDICAL DEVICES

(71) Applicant: Bard Shannon Limited, Humacao, PR (US)

(72) Inventors: Gideon Sturlesi, Kammo (IL); Guy Tomer, Modiin (IL); Aurelie Benaddi, Netanya (IL); Mary Hainrichson, Caesarea (IL); Amir Hadid, Binyamina (IL); Ofer Yatziv, Caesarea (IL)

(73) Assignee: Bard Shannon Limited, Humacao, PR (US)

( * ) Notice: Subject to any disclaimer, the term of this patent is extended or adjusted under 35 U.S.C. 154(b) by 296 days.

(21) Appl. No.: 16/508,356

(22) Filed: Jul. 11, 2019

(65) Prior Publication Data

US 2020/0155721 A1 May 21, 2020

Related U.S. Application Data

(60) Provisional application No. 62/696,872, filed on Jul. 12, 2018.

(51) Int. Cl.
*A61L 24/04* (2006.01)
*A61L 24/00* (2006.01)

(52) U.S. Cl.
CPC .......... *A61L 24/043* (2013.01); *A61L 24/0036* (2013.01)

(58) Field of Classification Search
CPC ............................ A61L 24/043; A61L 24/0036
See application file for complete search history.

(56) References Cited

U.S. PATENT DOCUMENTS

| | | |
|---|---|---|
| 1,394,654 A | 10/1921 | Tressler |
| 1,844,679 A | 2/1932 | Price |
| 1,873,580 A | 8/1932 | Hailwood |
| 1,950,483 A | 3/1934 | Christopher et al. |
| 2,048,499 A | 7/1936 | Gellednien |
| 2,126,305 A | 8/1938 | Babcok |
| 2,166,074 A | 7/1939 | Reichel |
| 2,398,004 A | 4/1946 | Houck et al. |
| 2,417,713 A | 3/1947 | Stein |
| 2,558,065 A | 6/1951 | Tice |
| 2,658,001 A | 11/1953 | Young |
| 2,719,145 A | 9/1955 | Skelton et al. |
| 2,803,548 A | 8/1957 | Hagetry |
| 2,914,444 A | 11/1959 | Smith |
| 3,220,845 A | 11/1965 | Fort |
| 3,600,482 A | 8/1971 | Salyer et al. |
| 3,939,001 A | 2/1976 | Clausi et al. |
| 3,953,566 A | 4/1976 | Gore |
| 3,988,479 A | 10/1976 | Stephan |
| 4,187,390 A | 2/1980 | Gore |
| 4,188,373 A | 2/1980 | Krezanoski |
| 4,188,465 A | 2/1980 | Schneider et al. |
| 4,224,348 A | 9/1980 | Hayashi |
| 4,344,181 A | 8/1982 | Baecklund |
| 4,426,443 A | 1/1984 | Shank |
| 4,478,822 A | 10/1984 | Haslam |
| 4,527,906 A | 7/1985 | Jezbera |
| 4,572,906 A | 2/1986 | Sparkes |
| 4,600,574 A | 7/1986 | Lindner et al. |
| 4,605,513 A | 8/1986 | DiMarchi |
| 4,651,725 A | 3/1987 | Kifune |
| 4,711,848 A | 12/1987 | Insley |
| 4,729,897 A | 3/1988 | Poppe |
| 4,837,379 A | 6/1989 | Weinberg |
| 4,889,920 A | 12/1989 | Mueller |
| 4,891,319 A | 1/1990 | Roser |
| 4,931,501 A | 6/1990 | Lai et al. |
| 4,948,540 A | 8/1990 | Nigam |
| 4,952,618 A | 8/1990 | Olsen |
| 4,971,954 A | 11/1990 | Brodsky |
| 4,985,250 A | 1/1991 | Bee et al. |
| 5,015,677 A | 5/1991 | Benedict et al. |
| 5,019,096 A | 5/1991 | Fox, Jr. et al. |
| 5,026,785 A | 6/1991 | Mage |
| 5,059,636 A | 10/1991 | Grenga |
| 5,147,344 A | 9/1992 | Sachau |
| 5,209,776 A | 5/1993 | Bass |
| 5,399,361 A | 3/1995 | Song |
| 5,428,014 A | 6/1995 | Labroo |
| 5,433,943 A | 7/1995 | Osipow |
| 5,441,193 A | 8/1995 | Gravener |
| 5,480,644 A | 1/1996 | Freed |
| 5,487,889 A | 1/1996 | Eckert et al. |
| 5,487,895 A | 1/1996 | Dapper |
| 5,490,984 A | 2/1996 | Freed |
| 5,503,638 A | 4/1996 | Cooper et al. |
| 5,508,202 A | 4/1996 | Enomoto |
| 5,525,335 A | 6/1996 | Kitahara et al. |
| 5,549,628 A | 8/1996 | Cooper et al. |
| 5,549,904 A | 8/1996 | Juergensen |
| 5,575,803 A | 11/1996 | Cooper et al. |
| 5,618,312 A | 4/1997 | Yui |
| 5,702,409 A | 12/1997 | Rayburn et al. |
| 5,736,132 A | 4/1998 | Juergensen |
| 5,752,965 A | 5/1998 | Francis et al. |
| 5,752,974 A | 5/1998 | Rhee |
| 5,810,855 A | 9/1998 | Rayburn |
| 5,834,232 A | 11/1998 | Bishop |
| 5,895,412 A | 4/1999 | Tucker |
| 5,931,165 A | 8/1999 | Reich |

(Continued)

FOREIGN PATENT DOCUMENTS

| | | |
|---|---|---|
| AU | 2002241280 C1 | 10/2002 |
| AU | 762855 B2 | 7/2003 |

(Continued)

OTHER PUBLICATIONS

Defail et al., Controlled release of bioactive doxorubicin from microspheres embedded within gelatin scaffolds. Journal of Biomedical Materials Research Part A. Dec. 1, 20065;79(4):954-62.

(Continued)

*Primary Examiner* — Shirley V Gembeh
(74) *Attorney, Agent, or Firm* — Wolf, Greenfield & Sacks, P.C.

(57) ABSTRACT

A biocompatible material for securing such implantable medical devices, for example by using an adhesive path.

20 Claims, 7 Drawing Sheets

(56) References Cited

U.S. PATENT DOCUMENTS

| | | | |
|---|---|---|---|
| 5,939,385 A | 8/1999 | Labroo | |
| 5,948,662 A | 9/1999 | Kobayashi | |
| 6,007,613 A | 12/1999 | Izoret | |
| 6,030,821 A | 2/2000 | Soeda | |
| 6,046,024 A | 4/2000 | Burton | |
| 6,047,861 A | 4/2000 | Vidal | |
| 6,054,122 A | 4/2000 | MacPhee et al. | |
| 6,063,061 A | 5/2000 | Wallace | |
| 6,066,325 A | 5/2000 | Wallace | |
| 6,083,524 A | 7/2000 | Sawhney | |
| 6,100,053 A | 8/2000 | Bech | |
| 6,107,401 A | 8/2000 | Dado et al. | |
| 6,117,425 A | 9/2000 | MacPhee et al. | |
| 6,121,013 A | 9/2000 | Yamaguchi | |
| 6,132,759 A | 10/2000 | Schacht | |
| 6,136,341 A | 10/2000 | Petito | |
| 6,156,330 A | 12/2000 | Tsukada | |
| 6,162,241 A | 12/2000 | Coury et al. | |
| 6,190,896 B1 | 2/2001 | Fraij | |
| 6,197,325 B1 | 3/2001 | MacPhee et al. | |
| 6,228,393 B1 | 5/2001 | DiCosmo | |
| 6,267,957 B1 | 7/2001 | Green | |
| 6,303,752 B1 | 10/2001 | Olsen | |
| 6,371,975 B2 | 4/2002 | Cruise | |
| 6,410,056 B1 | 6/2002 | Setterstrom et al. | |
| 6,413,742 B1 | 7/2002 | Olsen | |
| 6,420,148 B2 | 7/2002 | Yamaguchi | |
| 6,454,787 B1 | 9/2002 | Maddalo | |
| 6,458,386 B1 | 10/2002 | Schacht | |
| 6,461,849 B1 | 10/2002 | Olsen | |
| 6,465,001 B1 | 10/2002 | Hubbell | |
| 6,475,516 B2 | 11/2002 | DiCosmo | |
| 6,509,039 B1 | 1/2003 | Nies | |
| 6,527,751 B2 | 3/2003 | Fischer et al. | |
| 6,531,147 B2 | 3/2003 | Sawhney | |
| 6,544,227 B2 | 4/2003 | Sahatjian | |
| 6,559,119 B1 | 5/2003 | Burgess et al. | |
| 6,565,530 B2 | 5/2003 | Sahatjian et al. | |
| 6,576,685 B2 | 6/2003 | Stedronsky | |
| 6,599,323 B2 | 7/2003 | Melican et al. | |
| 6,605,066 B1 | 8/2003 | Gravagna et al. | |
| 6,608,040 B1 | 8/2003 | Lin et al. | |
| 6,610,043 B1 | 8/2003 | Ingenito | |
| 6,649,386 B2 | 11/2003 | Roser | |
| 6,656,193 B2 | 12/2003 | Grant et al. | |
| 6,663,594 B2 | 12/2003 | Sahatjian | |
| 6,682,760 B2 | 1/2004 | Noff | |
| 6,685,626 B2 | 2/2004 | Wironen | |
| 6,695,823 B1 | 2/2004 | Lina et al. | |
| 6,704,210 B1 | 3/2004 | Myers | |
| 6,706,690 B2 | 3/2004 | Reich | |
| 6,762,336 B1 | 7/2004 | Macphee | |
| 6,773,156 B2 | 8/2004 | Henning | |
| 6,833,258 B2 | 12/2004 | Yokoyama | |
| 6,848,281 B2 | 2/2005 | Ishihara et al. | |
| 6,852,330 B2 | 2/2005 | Bowman et al. | |
| 6,863,783 B2 | 3/2005 | Lin | |
| 6,875,796 B2 | 4/2005 | Stedronsky | |
| 6,884,428 B2 | 4/2005 | Binette et al. | |
| 6,887,974 B2 | 5/2005 | Pathak | |
| 6,914,169 B1 | 7/2005 | Oota et al. | |
| 6,939,358 B2 | 9/2005 | Palacios et al. | |
| 6,939,364 B1 | 9/2005 | Soltz et al. | |
| 6,974,862 B2 | 12/2005 | Ringeisen et al. | |
| 6,992,172 B1 | 1/2006 | Chang | |
| 7,019,191 B2 | 3/2006 | Looney | |
| 7,021,086 B2 | 4/2006 | Ory et al. | |
| 7,045,601 B2 | 5/2006 | Metzner | |
| 7,074,981 B2 | 7/2006 | Chalmers | |
| 7,108,876 B2 | 9/2006 | Grindstaff | |
| 7,109,163 B2 | 9/2006 | Pendharkar | |
| 7,129,210 B2 | 10/2006 | Lowinger | |
| 7,186,684 B2 | 3/2007 | Pendharkar | |
| 7,189,410 B1 | 3/2007 | Drohan et al. | |
| 7,196,054 B1 | 3/2007 | Drohan et al. | |
| 7,208,171 B2 | 4/2007 | Messersmith et al. | |
| 7,208,179 B1 | 4/2007 | Drohan et al. | |
| 7,214,765 B2 | 5/2007 | Ringeisen et al. | |
| 7,217,294 B2 | 5/2007 | Kusanagi et al. | |
| 7,220,836 B2 | 5/2007 | Roser | |
| 7,229,959 B1 | 6/2007 | Drohan et al. | |
| 7,241,730 B2 | 7/2007 | Hubbell | |
| 7,252,836 B2 | 8/2007 | Brown et al. | |
| 7,252,837 B2 | 8/2007 | Guo et al. | |
| 7,279,177 B2 | 10/2007 | Looney et al. | |
| 7,285,580 B2 | 10/2007 | Stedronsky | |
| 7,303,814 B2 | 12/2007 | Lamberti et al. | |
| 7,320,962 B2 | 1/2008 | Reich | |
| 7,347,850 B2 | 3/2008 | Sawhney | |
| 7,381,859 B2 | 6/2008 | Hunt et al. | |
| 7,435,425 B2 | 10/2008 | Qian | |
| 7,459,425 B2 | 12/2008 | Wan et al. | |
| 7,468,350 B2 | 12/2008 | Gong | |
| 7,485,323 B2 | 2/2009 | Dolphin et al. | |
| 7,547,446 B2 | 6/2009 | Qian et al. | |
| 7,575,740 B2 | 8/2009 | Molenberg et al. | |
| 7,662,409 B2 | 2/2010 | Masters | |
| 7,718,556 B2 | 5/2010 | Matsuda et al. | |
| 7,722,582 B2 | 5/2010 | Lina et al. | |
| 7,758,554 B2 | 7/2010 | Lina et al. | |
| 7,766,891 B2 | 8/2010 | McGurk | |
| 7,799,767 B2 | 9/2010 | Lamberti et al. | |
| 7,897,728 B2 | 3/2011 | Dolphin et al. | |
| 7,910,690 B2 | 3/2011 | Ringeisen et al. | |
| 7,923,003 B2 | 4/2011 | Speitling et al. | |
| 7,947,077 B2 | 5/2011 | Zehbe et al. | |
| 7,951,100 B2 | 5/2011 | Hunt et al. | |
| 7,963,944 B2 | 6/2011 | Sahatjian et al. | |
| 7,985,601 B2 | 7/2011 | Healy et al. | |
| 7,998,466 B2 | 8/2011 | Hadba | |
| 8,039,090 B2 | 10/2011 | Kawamura et al. | |
| 8,053,423 B2 | 11/2011 | Lamberti et al. | |
| 8,092,820 B2 | 1/2012 | Qian et al. | |
| 8,096,979 B2 | 1/2012 | Lina et al. | |
| 8,133,269 B2 | 3/2012 | Flechsenhar et al. | |
| 8,133,484 B2 * | 3/2012 | Preiss-Bloom | A61L 15/325 424/94.63 |
| 8,133,504 B2 * | 3/2012 | Kettlewell | A61L 15/58 424/443 |
| 8,187,210 B2 | 5/2012 | Hunt et al. | |
| 8,226,970 B2 | 7/2012 | Ahlers et al. | |
| 8,241,654 B2 | 8/2012 | Stopek | |
| 8,268,968 B2 | 9/2012 | Ooya et al. | |
| 8,282,912 B2 | 10/2012 | Molenberg et al. | |
| 8,283,322 B2 | 10/2012 | Slusarewicz et al. | |
| 8,293,530 B2 | 10/2012 | Burgess et al. | |
| 8,298,565 B2 | 10/2012 | Taylor et al. | |
| 8,298,606 B2 | 10/2012 | Healy et al. | |
| 8,323,352 B2 | 12/2012 | Friedman et al. | |
| 8,333,803 B2 | 12/2012 | Park et al. | |
| 8,334,249 B2 | 12/2012 | Belten-Casteel et al. | |
| 8,357,172 B2 | 1/2013 | Harper | |
| 8,367,388 B2 | 2/2013 | Bloom et al. | |
| 8,372,037 B2 | 2/2013 | Sahatjian et al. | |
| 8,377,466 B2 | 2/2013 | Sehl et al. | |
| 8,383,141 B2 | 2/2013 | Qian et al. | |
| 8,394,059 B2 | 3/2013 | Sahatjian et al. | |
| 8,435,552 B2 | 5/2013 | O'Brien et al. | |
| 8,440,209 B2 | 5/2013 | Speitling et al. | |
| 8,475,812 B2 | 7/2013 | Nur | |
| 8,496,971 B2 | 7/2013 | Gradl et al. | |
| 8,529,956 B2 | 9/2013 | Campbell et al. | |
| 8,529,958 B2 | 9/2013 | Campbell et al. | |
| 8,529,959 B2 | 9/2013 | Campbell et al. | |
| 8,529,960 B2 | 9/2013 | Campbell et al. | |
| 8,529,961 B2 | 9/2013 | Campbell et al. | |
| 8,535,705 B2 | 9/2013 | Pathak et al. | |
| 8,609,122 B2 | 12/2013 | Lamberti et al. | |
| 8,613,734 B2 | 12/2013 | Lina et al. | |
| 8,637,081 B2 | 1/2014 | Gaissmaier et al. | |
| 8,642,831 B2 | 2/2014 | Larsen et al. | |
| 8,664,202 B2 | 3/2014 | Lamberti et al. | |
| 8,672,903 B2 | 3/2014 | Hunt et al. | |
| 8,691,259 B2 | 4/2014 | Bowman et al. | |

(56) References Cited

U.S. PATENT DOCUMENTS

| | | |
|---|---|---|
| 8,697,136 B2 | 4/2014 | Kawaguchi et al. |
| 8,703,117 B2 | 4/2014 | Bloom et al. |
| 8,722,039 B2 | 5/2014 | Preiss-Bloom et al. |
| 8,741,354 B2 | 6/2014 | Johnson et al. |
| 8,758,429 B2 | 6/2014 | Taylor et al. |
| 8,778,422 B2 | 7/2014 | Oesser |
| 8,834,416 B2 | 9/2014 | Sahatjian et al. |
| 8,852,625 B2 | 10/2014 | DeYoung et al. |
| 8,871,267 B2 | 10/2014 | Masters |
| 8,877,705 B2 | 11/2014 | Larreta-Garde et al. |
| 8,883,184 B2 | 11/2014 | Hill et al. |
| 8,911,789 B2 | 12/2014 | Campbell et al. |
| 8,933,290 B2 | 1/2015 | Lefranc et al. |
| 8,957,050 B2 | 2/2015 | Lamberti et al. |
| 8,961,544 B2 * | 2/2015 | Komlos .................. A61L 15/38 606/151 |
| 8,999,376 B2 | 4/2015 | Ericson |
| 9,017,664 B2 | 4/2015 | Preiss-Bloom et al. |
| 9,044,456 B2 | 6/2015 | Preiss-Bloom |
| 9,066,991 B2 | 6/2015 | Preiss-Bloom |
| 9,072,724 B2 | 7/2015 | Hausmanns et al. |
| 9,101,686 B2 | 8/2015 | Nakamura et al. |
| 9,138,483 B2 | 9/2015 | O'Brien et al. |
| 9,149,511 B2 | 10/2015 | Wang et al. |
| 9,162,006 B2 | 10/2015 | Hoefinghoff et al. |
| 9,211,175 B2 | 12/2015 | Stopek et al. |
| 9,226,736 B2 | 1/2016 | Obermiller et al. |
| 9,265,858 B2 | 2/2016 | Larsen |
| 9,272,047 B2 | 3/2016 | Seong et al. |
| 9,289,533 B2 | 3/2016 | Schussler et al. |
| 9,295,751 B2 | 3/2016 | Gaissmaier et al. |
| 9,297,464 B1 | 3/2016 | Wang |
| 9,301,880 B2 | 4/2016 | Lina et al. |
| 9,308,242 B2 | 4/2016 | Murray |
| 9,351,819 B2 | 5/2016 | Harper |
| 9,352,067 B2 | 5/2016 | Ericson |
| 9,364,503 B2 | 6/2016 | Campbell et al. |
| 9,387,276 B2 | 7/2016 | Sun et al. |
| 9,393,267 B2 | 7/2016 | Han et al. |
| 9,415,135 B2 | 8/2016 | Healy et al. |
| 9,415,142 B2 | 8/2016 | DeYoung et al. |
| 9,421,306 B2 | 8/2016 | Park et al. |
| 9,433,700 B2 | 9/2016 | Basore et al. |
| 9,435,516 B2 | 9/2016 | Sundholm |
| 9,445,947 B2 | 9/2016 | Hunt et al. |
| 9,456,813 B2 | 10/2016 | Obermiller et al. |
| 9,486,338 B2 | 11/2016 | McClain et al. |
| 9,486,431 B2 | 11/2016 | McClain et al. |
| 9,499,728 B2 | 11/2016 | Taguchi et al. |
| 9,510,856 B2 | 12/2016 | McClain et al. |
| 9,517,287 B2 | 12/2016 | Hedrich et al. |
| 9,533,069 B2 | 1/2017 | Larsen et al. |
| 9,561,247 B2 | 2/2017 | Nguyen et al. |
| 9,572,556 B2 | 2/2017 | Obermiller et al. |
| 9,610,382 B2 | 4/2017 | Lamberti et al. |
| 9,623,146 B2 | 4/2017 | Lamberti et al. |
| 9,636,433 B2 * | 5/2017 | Iram ...................... A61P 17/02 |
| 9,655,988 B2 | 5/2017 | Iram et al. |
| 9,687,215 B2 | 6/2017 | Obermiller et al. |
| 9,717,820 B2 | 8/2017 | Wang et al. |
| 9,724,078 B2 | 8/2017 | Larsen et al. |
| 9,737,642 B2 | 8/2017 | McClain et al. |
| 9,737,645 B2 | 8/2017 | DeYoung et al. |
| 9,744,218 B2 | 8/2017 | Gaissmaier et al. |
| 9,775,729 B2 | 10/2017 | McClain et al. |
| 9,788,821 B2 | 10/2017 | Johnson et al. |
| 9,789,233 B2 | 10/2017 | McClain et al. |
| 9,827,117 B2 | 11/2017 | Taylor et al. |
| 9,833,541 B2 | 12/2017 | McCoy et al. |
| 9,849,213 B2 | 12/2017 | Murray |
| 9,872,934 B2 | 1/2018 | Hedrich et al. |
| 9,877,926 B2 | 1/2018 | Zilberman et al. |
| 9,919,080 B1 | 3/2018 | Chen et al. |
| 9,933,237 B2 | 4/2018 | Tarasoff |
| 9,950,093 B2 | 4/2018 | Zussman et al. |
| 9,956,311 B2 | 5/2018 | Ericson |
| 9,981,071 B2 | 5/2018 | McClain et al. |
| 9,981,072 B2 | 5/2018 | Taylor et al. |
| 9,987,400 B1 | 6/2018 | Chen et al. |
| 9,999,703 B2 | 6/2018 | Larsen |
| 10,034,969 B1 | 7/2018 | Chen et al. |
| 10,046,081 B2 | 8/2018 | Bowlin et al. |
| 10,064,973 B2 | 9/2018 | Taguchi |
| 10,111,980 B2 | 10/2018 | Larsen |
| 10,124,084 B2 | 11/2018 | Datt et al. |
| 10,143,471 B2 | 12/2018 | Ladet |
| 10,179,856 B2 | 1/2019 | Karrer et al. |
| 10,202,585 B2 | 2/2019 | Tomer et al. |
| 10,238,480 B2 | 3/2019 | Harper |
| 10,265,274 B2 | 4/2019 | Zilberman et al. |
| 10,265,436 B2 | 4/2019 | Lamberti et al. |
| 10,279,043 B2 | 5/2019 | Van Spreuwel-Goossens |
| 10,307,237 B2 | 6/2019 | Wang et al. |
| 10,314,951 B2 | 6/2019 | Chen et al. |
| 10,350,333 B2 | 7/2019 | McClain et al. |
| 10,350,391 B2 | 7/2019 | McClain et al. |
| 10,364,283 B2 | 7/2019 | Oesser et al. |
| 10,383,980 B2 | 8/2019 | Sun et al. |
| 10,420,857 B2 | 9/2019 | Ringeisen et al. |
| 2001/0018598 A1 | 8/2001 | Cruise |
| 2002/0015724 A1 | 2/2002 | Yang |
| 2002/0049503 A1 * | 4/2002 | Milbocker .............. A61L 27/18 623/23.72 |
| 2003/0008831 A1 | 1/2003 | Yang |
| 2003/0022832 A1 | 1/2003 | Montero Garcia |
| 2003/0035786 A1 | 2/2003 | Hendriks |
| 2003/0120284 A1 | 6/2003 | Palacios et al. |
| 2003/0135238 A1 | 7/2003 | Milbocker |
| 2003/0175410 A1 | 9/2003 | Campbell et al. |
| 2003/0219857 A1 | 11/2003 | Chou |
| 2003/0232944 A1 | 12/2003 | Fehr et al. |
| 2004/0093029 A1 | 5/2004 | Zubik et al. |
| 2004/0106344 A1 | 6/2004 | Looney |
| 2004/0131728 A1 | 7/2004 | Ootzuka et al. |
| 2005/0113937 A1 | 5/2005 | Binette et al. |
| 2005/0129733 A1 | 6/2005 | Milbocker |
| 2005/0147646 A1 | 7/2005 | Nilsson |
| 2005/0153090 A1 | 7/2005 | Marchitto et al. |
| 2005/0209441 A1 | 9/2005 | Lile |
| 2005/0238683 A1 | 10/2005 | Adhikari et al. |
| 2005/0249839 A1 | 11/2005 | Ishida |
| 2005/0271727 A1 | 12/2005 | Yao |
| 2006/0002585 A1 | 1/2006 | Yang et al. |
| 2006/0025785 A1 | 2/2006 | Cully et al. |
| 2006/0078962 A1 | 4/2006 | Chen et al. |
| 2006/0100138 A1 | 5/2006 | Olsen |
| 2006/0155234 A1 | 7/2006 | Macphee |
| 2006/0258560 A1 | 11/2006 | Yang et al. |
| 2006/0269590 A1 | 11/2006 | Trotter |
| 2006/0286165 A1 | 12/2006 | Ge et al. |
| 2007/0021703 A1 | 1/2007 | McCarthy |
| 2007/0082023 A1 | 4/2007 | Hopman |
| 2007/0128152 A1 | 6/2007 | Hadba |
| 2007/0172432 A1 | 7/2007 | Stopek |
| 2007/0246505 A1 | 10/2007 | Pace-Florida et al. |
| 2007/0275027 A1 | 11/2007 | Wen et al. |
| 2008/0161757 A1 | 7/2008 | Nayak |
| 2008/0187591 A1 | 8/2008 | Rhee |
| 2008/0195037 A1 | 8/2008 | Hissong |
| 2008/0213243 A1 | 9/2008 | Preiss-Bloom |
| 2008/0260801 A1 | 10/2008 | Ahlers et al. |
| 2008/0286376 A1 | 11/2008 | Qian |
| 2009/0099579 A1 | 4/2009 | Nentwick et al. |
| 2009/0175946 A1 | 7/2009 | Gaissmaier et al. |
| 2009/0191269 A1 | 7/2009 | Gaissmaier et al. |
| 2009/0316588 A1 | 12/2009 | Nakamura et al. |
| 2010/0008989 A1 | 1/2010 | Attar et al. |
| 2010/0063459 A1 | 3/2010 | Preiss-Bloom |
| 2010/0239635 A1 | 9/2010 | McClain et al. |
| 2011/0021964 A1 | 1/2011 | Larsen |
| 2011/0110882 A1 | 5/2011 | Preiss-Bloom et al. |
| 2012/0059411 A1 | 3/2012 | Sun et al. |
| 2012/0209319 A1 | 8/2012 | Bianco-Peled |
| 2012/0226211 A1 | 9/2012 | Preiss-Bloom |

(56) References Cited

U.S. PATENT DOCUMENTS

| | | |
|---|---|---|
| 2012/0270810 A1 | 10/2012 | Preiss-Bloom et al. |
| 2012/0329132 A1 | 12/2012 | Bloom et al. |
| 2013/0039899 A1 | 2/2013 | Preiss-Bloom et al. |
| 2013/0131701 A1 | 5/2013 | Komlos et al. |
| 2013/0324455 A1 | 12/2013 | Blattner et al. |
| 2014/0314732 A1 | 10/2014 | Preiss-Bloom |
| 2015/0132362 A1 | 5/2015 | Hoefinghoff et al. |
| 2015/0133377 A1 | 5/2015 | Mayes et al. |
| 2015/0196683 A1 | 7/2015 | Iram et al. |
| 2015/0273103 A1 | 10/2015 | Iram et al. |
| 2015/0283287 A1 | 10/2015 | Agarwal et al. |
| 2015/0291939 A1 | 10/2015 | Tomer et al. |
| 2015/0328363 A1 | 11/2015 | Leimer et al. |
| 2016/0008508 A1 | 1/2016 | Nakahara et al. |
| 2016/0015537 A1 | 1/2016 | Taylor et al. |
| 2016/0045198 A1 | 2/2016 | Bachrach |
| 2016/0051618 A1 | 2/2016 | Hausmanns et al. |
| 2016/0151062 A1 | 6/2016 | Bachrach |
| 2016/0178611 A1 | 6/2016 | Han et al. |
| 2016/0265028 A1 | 9/2016 | Kim et al. |
| 2016/0271290 A1 | 9/2016 | Humayun et al. |
| 2016/0287754 A1 | 10/2016 | Han et al. |
| 2016/0331862 A1 | 11/2016 | Basore et al. |
| 2016/0354253 A1 | 12/2016 | Hunt et al. |
| 2016/0355859 A1 | 12/2016 | Johansen et al. |
| 2017/0119925 A1 | 5/2017 | Healy et al. |
| 2017/0136154 A1 | 5/2017 | Ferrari et al. |
| 2017/0182209 A1 | 6/2017 | Branco Da Cunha et al. |
| 2017/0245847 A1 | 8/2017 | Obermiller et al. |
| 2017/0311939 A1 | 11/2017 | Larsen et al. |
| 2017/0319193 A1 | 11/2017 | Pulapura et al. |
| 2017/0319746 A1 | 11/2017 | Lutolf et al. |
| 2017/0319754 A1 | 11/2017 | Pulapura et al. |
| 2017/0348894 A1 | 12/2017 | Wimmer et al. |
| 2017/0368224 A1 | 12/2017 | Griffin et al. |
| 2018/0000996 A1 | 1/2018 | McClain et al. |
| 2018/0021473 A1 | 1/2018 | Yliperttula et al. |
| 2018/0078671 A1 | 3/2018 | Griffin et al. |
| 2018/0092762 A1 | 4/2018 | Taylor et al. |
| 2018/0104377 A1 | 4/2018 | Hedrich et al. |
| 2018/0207316 A1 | 7/2018 | Murray |
| 2018/0214602 A1 | 8/2018 | Chen et al. |
| 2018/0243465 A1 | 8/2018 | Qin et al. |
| 2018/0256641 A1 | 9/2018 | Attar |
| 2018/0258960 A9 | 9/2018 | Ghahary et al. |
| 2018/0272043 A1 | 9/2018 | Taylor et al. |
| 2018/0311376 A1 | 11/2018 | Wurst et al. |
| 2018/0344891 A1 | 12/2018 | Bowlin et al. |
| 2018/0361020 A1 | 12/2018 | Nakamura et al. |
| 2019/0010963 A9 | 1/2019 | Ghahary et al. |
| 2019/0015546 A1 | 1/2019 | Larsen |
| 2019/0030218 A1 | 1/2019 | Pulapura et al. |
| 2019/0060510 A1 | 2/2019 | Ericson |
| 2019/0060522 A1 | 2/2019 | Frey et al. |
| 2019/0083676 A1 | 3/2019 | Zilberman et al. |
| 2019/0111190 A1 | 4/2019 | DeYoung et al. |
| 2019/0125936 A1 | 5/2019 | Preiss-Bloom et al. |
| 2019/0134264 A1 | 5/2019 | Wu et al. |
| 2019/0151399 A1 | 5/2019 | Hausmanns et al. |
| 2019/0151497 A1 | 5/2019 | Griffin et al. |
| 2019/0184062 A1 | 6/2019 | Park et al. |
| 2019/0192727 A1 | 6/2019 | Basore et al. |
| 2019/0192728 A1 | 6/2019 | Basore et al. |
| 2019/0201536 A1 | 7/2019 | Van Spreuwel-Goosens |
| 2019/0209742 A1 | 7/2019 | McClain et al. |
| 2019/0211296 A1 | 7/2019 | Allbritton |
| 2019/0224364 A1 | 7/2019 | Bacchetta et al. |
| 2019/0247175 A1 | 8/2019 | Wang et al. |
| 2019/0247537 A1 | 8/2019 | Taguchi |
| 2019/0262430 A1 | 8/2019 | Oesser et al. |
| 2019/0262510 A1 | 8/2019 | Chen et al. |
| 2019/0275207 A1 | 9/2019 | Park et al. |
| 2020/0016295 A1 | 1/2020 | Tomer et al. |
| 2020/0276362 A1 | 9/2020 | Tomer et al. |
| 2022/0126000 A1 | 4/2022 | Preiss-Bloom et al. |
| 2022/0331492 A1 | 10/2022 | Tomer et al. |

FOREIGN PATENT DOCUMENTS

| | | |
|---|---|---|
| AU | 762895 B2 | 7/2003 |
| AU | 2003213253 A1 | 9/2003 |
| AU | 2003215330 A1 | 9/2003 |
| AU | 2003226688 A1 | 10/2003 |
| AU | 2003204986 A1 | 1/2004 |
| AU | 772880 B2 | 5/2004 |
| AU | 2003204989 A1 | 10/2004 |
| AU | 779655 B2 | 2/2005 |
| AU | 2004285480 A1 | 5/2005 |
| AU | 2006242214 A1 | 11/2006 |
| AU | 2006254328 A1 | 12/2006 |
| AU | 2002345846 B2 | 8/2007 |
| AU | 2007213923 A1 | 8/2007 |
| AU | 2007243268 A1 | 11/2007 |
| AU | 2007320018 A1 | 5/2008 |
| AU | 2008212526 A1 | 8/2008 |
| AU | 2008224180 A1 | 9/2008 |
| AU | 2008277355 A1 | 1/2009 |
| AU | 2008279578 A1 | 1/2009 |
| AU | 2009251504 A1 | 12/2009 |
| AU | 2009259828 A1 | 12/2009 |
| AU | 2009259835 A1 | 12/2009 |
| AU | 2009270849 A1 | 1/2010 |
| AU | 2009316594 A1 | 5/2010 |
| AU | 2011232760 A1 | 10/2011 |
| AU | 2006270221 B2 | 1/2012 |
| AU | 2011256902 A1 | 1/2012 |
| AU | 2012201042 A1 | 3/2012 |
| AU | 2012203577 A1 | 7/2012 |
| AU | 2010262058 B2 | 8/2013 |
| AU | 2010266266 B2 | 10/2014 |
| AU | 2013275758 B2 | 3/2015 |
| AU | 2015200571 A1 | 4/2015 |
| AU | 2015203152 A1 | 7/2015 |
| AU | 2010264800 B2 | 8/2015 |
| AU | 2013257459 B2 | 9/2015 |
| AU | 2011331466 B2 | 2/2016 |
| AU | 2012275858 B2 | 2/2016 |
| AU | 2010243527 B2 | 4/2016 |
| AU | 2013214974 B2 | 12/2016 |
| AU | 2012344135 B2 | 1/2017 |
| AU | 2015289474 A1 | 2/2017 |
| AU | 2017200794 A1 | 3/2017 |
| AU | 2012330450 B2 | 4/2017 |
| AU | 2014267613 B2 | 6/2017 |
| AU | 2016214910 A1 | 8/2017 |
| AU | 2016241383 A1 | 10/2017 |
| AU | 2014283170 B2 | 11/2017 |
| AU | 2014361291 B2 | 11/2017 |
| AU | 2016347548 A1 | 2/2018 |
| AU | 2013343685 B2 | 3/2018 |
| AU | 2017320520 A1 | 3/2019 |
| AU | 2017394923 A1 | 8/2019 |
| AU | 2018212908 A1 | 8/2019 |
| AU | 2015301688 B2 | 10/2019 |
| AU | 2016313773 B2 | 11/2020 |
| AU | 2016265286 B2 | 1/2021 |
| CA | 896965 A | 4/1972 |
| CA | 2351341 A1 | 6/2000 |
| CA | 2353642 A1 | 6/2000 |
| CA | 2367460 A1 | 10/2000 |
| CA | 2408305 A1 | 11/2001 |
| CA | 2312558 A1 | 12/2001 |
| CA | 2439904 A1 | 9/2002 |
| CA | 2623603 A1 | 9/2002 |
| CA | 2441480 A1 | 10/2002 |
| CA | 2453592 A1 | 1/2003 |
| CA | 2476653 A1 | 9/2003 |
| CA | 2476656 A1 | 9/2003 |
| CA | 2478253 A1 | 10/2003 |
| CA | 2433968 A1 | 12/2003 |
| CA | 2433964 A1 | 9/2004 |
| CA | 2536094 A1 | 3/2005 |

(56) References Cited

FOREIGN PATENT DOCUMENTS

| | | |
|---|---|---|
| CA | 2543255 A1 | 5/2005 |
| CA | 2583561 A1 | 4/2006 |
| CA | 2606445 A1 | 11/2006 |
| CA | 2833585 A1 | 11/2006 |
| CA | 2599059 A1 | 12/2006 |
| CA | 2615452 A1 | 1/2007 |
| CA | 2637794 A1 | 8/2007 |
| CA | 2650690 A1 | 11/2007 |
| CA | 2996768 A1 | 11/2007 |
| CA | 2664866 A1 | 5/2008 |
| CA | 2679712 A1 | 7/2008 |
| CA | 2677992 A1 | 8/2008 |
| CA | 2677997 A1 | 9/2008 |
| CA | 2684482 A1 | 10/2008 |
| CA | 2691412 A1 | 1/2009 |
| CA | 2701187 A1 | 1/2009 |
| CA | 2716872 A1 | 9/2009 |
| CA | 2721832 A1 | 12/2009 |
| CA | 2728513 A1 | 12/2009 |
| CA | 2734650 A1 | 12/2009 |
| CA | 2730995 A1 | 1/2010 |
| CA | 2946195 A1 | 1/2010 |
| CA | 2744232 A1 | 5/2010 |
| CA | 2756307 A1 | 9/2010 |
| CA | 2756386 A1 | 9/2010 |
| CA | 2757276 A1 | 10/2010 |
| CA | 2759015 A1 | 10/2010 |
| CA | 2765117 A1 | 12/2010 |
| CA | 2766390 A1 | 1/2011 |
| CA | 3000888 A1 | 1/2011 |
| CA | 2784432 A1 | 7/2011 |
| CA | 2816900 A1 | 5/2012 |
| CA | 2826581 A1 | 8/2012 |
| CA | 2840290 A1 | 1/2013 |
| CA | 2853356 A1 | 5/2013 |
| CA | 2854160 A1 | 5/2013 |
| CA | 2854856 A1 | 6/2013 |
| CA | 2864075 A1 | 8/2013 |
| CA | 2899126 A1 | 8/2013 |
| CA | 2874290 A1 | 12/2013 |
| CA | 2616865 C | 7/2014 |
| CA | 2928222 A1 | 11/2014 |
| CA | 2912357 A1 | 12/2014 |
| CA | 2928963 A1 | 6/2015 |
| CA | 2955357 A1 | 1/2016 |
| CA | 2956077 A1 | 2/2016 |
| CA | 2974209 A1 | 8/2016 |
| CA | 2981587 A1 | 10/2016 |
| CA | 2985537 A1 | 11/2016 |
| CA | 2996853 A1 | 3/2017 |
| CA | 3002296 A1 | 4/2017 |
| CA | 2993415 A1 | 5/2017 |
| CA | 3052250 A1 | 2/2018 |
| CA | 3035281 A1 | 3/2018 |
| CA | 3051055 A1 | 7/2018 |
| CN | 1161790 A | 10/1997 |
| CN | 1617735 A | 5/2005 |
| CN | 1646029 A | 7/2005 |
| CN | 102719411 A | 10/2012 |
| CN | 102727929 A | 10/2012 |
| CN | 103118713 A | 5/2013 |
| CN | 103263688 A | 8/2013 |
| CN | 103816562 A | 5/2014 |
| CN | 105664232 A | 6/2016 |
| CN | 105749350 A | 7/2016 |
| CN | 106421884 A | 2/2017 |
| CN | 106729957 A | 5/2017 |
| CN | 107261216 A | 10/2017 |
| CN | 108310448 A | 7/2018 |
| DE | 10 2005 054 940 A1 | 5/2007 |
| DE | 60125164 T2 | 9/2007 |
| DE | 10 2006 033 168 A1 | 1/2008 |
| EP | 0 073 908 A1 | 3/1983 |
| EP | 0 185 494 B1 | 6/1986 |
| EP | 0 302 953 A1 | 2/1989 |
| EP | 0 636 378 A1 | 2/1995 |
| EP | 0 707 474 A1 | 4/1996 |
| EP | 0 726 317 A2 | 8/1996 |
| EP | 0 745 670 A1 | 12/1996 |
| EP | 0 777 726 A1 | 6/1997 |
| EP | 0 815 742 A2 | 1/1998 |
| EP | 0 871 712 A1 | 10/1998 |
| EP | 0 876 166 A1 | 11/1998 |
| EP | 0 927 053 A1 | 7/1999 |
| EP | 0 947 142 A2 | 10/1999 |
| EP | 0 982 038 A1 | 3/2000 |
| EP | 1 267 826 A1 | 1/2003 |
| EP | 1 267 876 A1 | 1/2003 |
| EP | 1 288 264 A1 | 3/2003 |
| EP | 1 003 568 B1 | 4/2003 |
| EP | 1 372 492 A1 | 1/2004 |
| EP | 1 374 699 B1 | 1/2004 |
| EP | 1 378 255 A2 | 1/2004 |
| EP | 1 073 342 B1 | 6/2004 |
| EP | 1 462 122 A1 | 9/2004 |
| EP | 1 494 730 A1 | 1/2005 |
| EP | 1 263 327 B1 | 8/2005 |
| EP | 1 574 229 A1 | 9/2005 |
| EP | 1 284 777 B1 | 4/2006 |
| EP | 1 642 599 A1 | 4/2006 |
| EP | 1 677 846 A2 | 7/2006 |
| EP | 1 695 722 A1 | 8/2006 |
| EP | 1 414 370 B1 | 4/2007 |
| EP | 1 803 417 A1 | 7/2007 |
| EP | 1 857 494 A1 | 11/2007 |
| EP | 1 476 204 B1 | 10/2008 |
| EP | 1 987 850 A1 | 11/2008 |
| EP | 1 476 202 B1 | 1/2009 |
| EP | 2 033 662 A1 | 3/2009 |
| EP | 2 045 319 A1 | 4/2009 |
| EP | 2 050 474 B1 | 4/2009 |
| EP | 1 124 590 B1 | 6/2009 |
| EP | 2 073 788 A2 | 7/2009 |
| EP | 2 100 914 B1 | 9/2009 |
| EP | 2 117 617 A2 | 11/2009 |
| EP | 2 133 069 A1 | 12/2009 |
| EP | 2 138 049 A1 | 12/2009 |
| EP | 1 948 260 B1 | 1/2010 |
| EP | 2 146 758 A1 | 1/2010 |
| EP | 2 168 610 A2 | 3/2010 |
| EP | 2 196 193 B1 | 6/2010 |
| EP | 2 255 837 A1 | 12/2010 |
| EP | 2 173 274 B1 | 3/2011 |
| EP | 1 796 751 B1 | 5/2011 |
| EP | 2 037 974 B1 | 5/2011 |
| EP | 2 182 994 B1 | 6/2011 |
| EP | 2 349 089 A2 | 8/2011 |
| EP | 2 037 972 B1 | 9/2011 |
| EP | 2 126 166 B1 | 9/2011 |
| EP | 2 094 323 B1 | 11/2011 |
| EP | 2 404 571 A1 | 1/2012 |
| EP | 1 169 071 B1 | 2/2012 |
| EP | 2 410 954 A2 | 2/2012 |
| EP | 2 411 083 A2 | 2/2012 |
| EP | 1 708 755 B1 | 3/2012 |
| EP | 2 453 834 A1 | 5/2012 |
| EP | 2 144 641 B1 | 7/2012 |
| EP | 2 487 206 A2 | 8/2012 |
| EP | 2 259 803 B1 | 9/2012 |
| EP | 2 517 738 A1 | 10/2012 |
| EP | 2 536 094 A1 | 12/2012 |
| EP | 2 543 398 A1 | 1/2013 |
| EP | 2 111 239 B1 | 3/2013 |
| EP | 2 424 886 B1 | 4/2013 |
| EP | 2 623 129 A1 | 8/2013 |
| EP | 2 626 086 A1 | 8/2013 |
| EP | 2 644 114 A2 | 10/2013 |
| EP | 2 675 492 A1 | 12/2013 |
| EP | 1 885 771 B1 | 2/2014 |
| EP | 2 771 027 A1 | 9/2014 |

(56) References Cited

FOREIGN PATENT DOCUMENTS

| | | |
|---|---|---|
| EP | 2 310 459 B1 | 10/2014 |
| EP | 2 442 835 B1 | 12/2014 |
| EP | 2 809 362 A2 | 12/2014 |
| EP | 2 550 034 B1 | 1/2015 |
| EP | 2 826 494 A1 | 1/2015 |
| EP | 2 455 109 B1 | 2/2015 |
| EP | 2 842 576 A1 | 3/2015 |
| EP | 2 019 657 B1 | 5/2015 |
| EP | 2 268 715 B1 | 7/2015 |
| EP | 2 307 071 B1 | 8/2015 |
| EP | 2 825 216 B1 | 8/2015 |
| EP | 2 946 795 A1 | 11/2015 |
| EP | 2 952 214 A1 | 12/2015 |
| EP | 1 984 032 B1 | 1/2016 |
| EP | 2 962 703 A1 | 1/2016 |
| EP | 2 836 558 B1 | 5/2016 |
| EP | 2 916 855 B1 | 7/2016 |
| EP | 3 050 579 A1 | 8/2016 |
| EP | 2 358 409 B1 | 1/2017 |
| EP | 1 981 553 B1 | 3/2017 |
| EP | 2 190 968 B1 | 6/2017 |
| EP | 2 776 052 B1 | 6/2017 |
| EP | 2 640 352 B1 | 8/2017 |
| EP | 3 210 634 A1 | 8/2017 |
| EP | 2 726 115 B1 | 9/2017 |
| EP | 1 656 081 B1 | 10/2017 |
| EP | 3 229 853 A1 | 10/2017 |
| EP | 2 445 510 B1 | 12/2017 |
| EP | 2 680 713 B1 | 12/2017 |
| EP | 3 253 417 A1 | 12/2017 |
| EP | 1 185 288 B1 | 1/2018 |
| EP | 2 157 983 B1 | 1/2018 |
| EP | 2 419 058 B1 | 2/2018 |
| EP | 3 281 605 A1 | 2/2018 |
| EP | 2 271 294 B1 | 3/2018 |
| EP | 2 785 420 B1 | 3/2018 |
| EP | 2 111 184 B1 | 7/2018 |
| EP | 1 909 973 B1 | 8/2018 |
| EP | 2 849 811 B1 | 8/2018 |
| EP | 3 079 731 B1 | 8/2018 |
| EP | 3 360 586 A1 | 8/2018 |
| EP | 3 364 948 A1 | 8/2018 |
| EP | 3 366 326 A1 | 8/2018 |
| EP | 1 876 965 B1 | 9/2018 |
| EP | 3 370 793 A2 | 9/2018 |
| EP | 3 445 412 A1 | 2/2019 |
| EP | 2 313 122 B1 | 3/2019 |
| EP | 3 452 122 A1 | 3/2019 |
| EP | 3 452 125 A1 | 3/2019 |
| EP | 3 452 126 A1 | 3/2019 |
| EP | 3 470 094 A1 | 4/2019 |
| EP | 3 491 122 A1 | 6/2019 |
| EP | 3 506 929 A1 | 7/2019 |
| EP | 3 180 045 B1 | 2/2020 |
| EP | 3 122 300 B1 | 3/2020 |
| EP | 3 010 419 B1 | 5/2020 |
| EP | 2 448 497 B1 | 12/2020 |
| EP | 2 996 710 B1 | 3/2021 |
| EP | 3 218 171 B1 | 6/2021 |
| GB | 2535117 A | 8/2016 |
| GB | 2549522 A | 10/2017 |
| IL | 200295 A | 6/2015 |
| IL | 201550 A | 10/2015 |
| IN | 258325 B | 1/2014 |
| IN | 289218 B | 11/2017 |
| IN | 292611 B | 2/2018 |
| IN | 292763 B | 2/2018 |
| IN | 294277 B | 3/2018 |
| IN | 296955 B | 5/2018 |
| IN | 301188 B | 9/2018 |
| IN | 311099 B | 4/2019 |
| IN | 312338 | 5/2019 |
| JP | 2204407 A | 8/1990 |
| JP | 2255888 A | 10/1990 |
| JP | H03-095109 A | 4/1991 |
| JP | H07-215894 A | 8/1995 |
| JP | H07-227228 A | 8/1995 |
| JP | H07-328108 | 12/1995 |
| JP | H10-510183 | 10/1998 |
| JP | 2002-515300 A | 5/2002 |
| JP | 2004-269542 A | 9/2004 |
| JP | 2004-283371 A | 10/2004 |
| JP | 2004-531534 A | 10/2004 |
| JP | 2005-152653 A | 6/2005 |
| JP | 2006-503612 A | 2/2006 |
| JP | 3916516 B2 | 5/2007 |
| JP | 2007-167655 A | 7/2007 |
| JP | 2007-537314 A | 12/2007 |
| JP | 2009-529589 A | 8/2009 |
| JP | 2009-542384 A | 12/2009 |
| JP | 2010-521994 A | 7/2010 |
| JP | 2011-036320 A | 2/2011 |
| JP | 2011-200651 A | 10/2011 |
| JP | 2013-503673 A | 2/2013 |
| JP | 5475283 B2 | 2/2014 |
| NZ | 535369 A | 2/2006 |
| NZ | 535136 A | 3/2006 |
| SG | 183035 A1 | 8/2012 |
| SG | 192523 A1 | 8/2013 |
| SG | 192524 A1 | 8/2013 |
| WO | WO 93/20837 A1 | 10/1993 |
| WO | WO 96/17929 A1 | 6/1996 |
| WO | WO 96/40791 A1 | 12/1996 |
| WO | WO 97/10701 A1 | 3/1997 |
| WO | WO 97/22372 A1 | 6/1997 |
| WO | WO 97/28834 A1 | 8/1997 |
| WO | WO 97/29715 A1 | 8/1997 |
| WO | WO 97/37694 A1 | 10/1997 |
| WO | WO 97/40701 A1 | 11/1997 |
| WO | WO 97/41899 A1 | 11/1997 |
| WO | WO 98/00180 A1 | 1/1998 |
| WO | WO 98/35026 A1 | 8/1998 |
| WO | WO 99/10952 A1 | 3/1999 |
| WO | WO 99/57254 A1 | 11/1999 |
| WO | WO 00/22103 A1 | 4/2000 |
| WO | WO 00/76533 A1 | 12/2000 |
| WO | WO 01/15750 A1 | 3/2001 |
| WO | WO 01/85224 A1 | 11/2001 |
| WO | WO 02/085422 A1 | 10/2002 |
| WO | WO 02/098937 A1 | 12/2002 |
| WO | WO 03/011352 A1 | 2/2003 |
| WO | WO 03/072155 A1 | 9/2003 |
| WO | WO 03/072157 A1 | 9/2003 |
| WO | WO 03/074004 A2 | 9/2003 |
| WO | WO 03/080144 A1 | 10/2003 |
| WO | WO 03/086493 A1 | 10/2003 |
| WO | WO 2004/004875 A2 | 1/2004 |
| WO | WO 2004/014969 A1 | 2/2004 |
| WO | WO 2004/024195 A1 | 3/2004 |
| WO | WO 2004/028404 A2 | 4/2004 |
| WO | WO 2004/029096 A2 | 4/2004 |
| WO | WO 2004/098671 A2 | 11/2004 |
| WO | WO 2004/105485 A2 | 12/2004 |
| WO | WO 2005/006991 A2 | 1/2005 |
| WO | WO 2005/016170 A2 | 2/2005 |
| WO | WO 2005/061701 A1 | 7/2005 |
| WO | WO 2005/092204 A2 | 10/2005 |
| WO | WO 2006/014567 A2 | 2/2006 |
| WO | WO 2006/014568 A2 | 2/2006 |
| WO | WO 2006/016809 A1 | 2/2006 |
| WO | WO 2006/027622 A2 | 3/2006 |
| WO | WO 2006/056700 A2 | 6/2006 |
| WO | WO 2006/086479 A2 | 8/2006 |
| WO | WO 2006/128685 A2 | 12/2006 |
| WO | WO 2006/134148 A2 | 12/2006 |
| WO | WO 2007/008229 A2 | 1/2007 |
| WO | WO 2007/025726 A1 | 3/2007 |
| WO | WO 2007/057175 A2 | 5/2007 |
| WO | WO 2007/122232 A2 | 11/2007 |
| WO | WO 2007/123350 A1 | 11/2007 |
| WO | WO 2007/126411 A2 | 11/2007 |
| WO | WO 2007/134118 A2 | 11/2007 |
| WO | WO 2008/000655 A2 | 1/2008 |
| WO | WO 2008/006544 A2 | 1/2008 |

(56) References Cited

FOREIGN PATENT DOCUMENTS

| | | | |
|---|---|---|---|
| WO | WO 2008/006545 A2 | 1/2008 |
| WO | WO 2008/016983 A2 | 2/2008 |
| WO | WO 2008/073938 A2 | 6/2008 |
| WO | WO 2008/076407 | * | 6/2008 |
| WO | WO 2008/103891 A2 | 8/2008 |
| WO | WO 2008/103981 A2 | 8/2008 |
| WO | WO 2009/012882 A1 | 1/2009 |
| WO | WO 2009/026158 A2 | 2/2009 |
| WO | WO 2009/036014 A2 | 3/2009 |
| WO | WO 2009/075329 A1 | 6/2009 |
| WO | WP 2009/073193 A2 | 6/2009 |
| WO | WO 2009/105614 A2 | 8/2009 |
| WO | WO 2009/153748 A2 | 12/2009 |
| WO | WO 2009/153750 A2 | 12/2009 |
| WO | WO 2009/153751 A2 | 12/2009 |
| WO | WO 2010/027417 A2 | 3/2010 |
| WO | WO 2010/145817 A2 | 12/2010 |
| WO | WO 2010/146582 A2 | 12/2010 |
| WO | WO 2011/077388 A1 | 6/2011 |
| WO | WO 2011/079336 A1 | 7/2011 |
| WO | WO 2017/223462 A1 | 12/2017 |
| WO | WO 2018/136205 A1 | 7/2018 |
| WO | WO 2018/185302 A1 | 10/2018 |
| WO | WO2019003224 | * | 1/2019 |
| WO | WO 2019/086952 A1 | 5/2019 |

OTHER PUBLICATIONS

McBain et al., On adhesives and adhesive action. The Journal of Physical Chemistry. 1925;29(2):188-204.

Song et al., A novel human-like collagen hydrogel scaffold with porous structure and sponge-like properties. Polymers. Dec. 2017;9(12):638.

Yang et al., Enzymatically crosslinked gelatin hydrogel promotes the proliferation of adipose tissue-derived stromal cells. PeerJ. Sep. 27, 2016;4:e2497.

U.S. Appl. No. 17/741,358, filed May 10, 2022, Preiss-Bloom et al.

Liu et al., Study of antioxidant effects on malignant glioma cells by constructing a tumor-microvascular structure on microchip. Anal Chim Acta. Jul. 25, 2017;978:1-9. doi: 10.1016/j.aca.2017.05.009. Epub May 16, 2017. Abstract only.

Taylor et al., Investigating processing techniques for bovine gelatin electrospun scaffolds for bone tissue regeneration. J Biomed Mater Res B Appl Biomater. Jul. 2017;105(5):1131-1140. doi: 10.1002/jbm.b.33622. Epub Mar. 28, 2016. Abstract only.

Ito et al., Transglutaminase-mediated gelatin matrices incorporating cell adhesion factors as a biomaterial for tissue engineering. J Biosci Bioeng. 2003;95(2):196-9.

Marrella et al., 3D Porous Gelatin/PVA Hydrogel as Meniscus Substitute Using Alginate Micro-Particles as Porogens. Polymers (Basel). Apr. 1, 2018;10(4):380. doi: 10.3390/polym10040380.

U.S. Appl. No. 16/099,834, filed Nov. 8, 2018, Preiss-Bloom et al.
U.S. Appl. No. 17/520,561, filed Nov. 5, 2021, Preiss-Bloom et al.
U.S. Appl. No. 16/650,956, filed Mar. 26, 2020, Tomer et al.
U.S. Appl. No. 16/508,343, filed Jul. 11, 2019, Tomer et al.

* cited by examiner

SECURING IMPLANTS AND MEDICAL DEVICES

FIELD OF THE INVENTION

The present invention relates to the use of biocompatible adhesive materials for seeming a foreign body or an external device to a tissue, and in particular to such adhesive materials that feature enzymatically crosslinked gelatin matrix.

BACKGROUND OF THE INVENTION

Currently, medical devices that are implanted in the body are secured to the implantation site using mechanical fixation means, e.g. sutures or tacks or using tissue adhesives, most of them are based on cyanoacrylate chemistries, which are known to be toxic. Interest in soft tissue adhesives is growing because of the desire to replace or supplement sutures for wound closure (Glickman M et al) and the trends toward less invasive and cosmetic surgeries (Tissue Adhesives in Clinical Medicine).

Today, grafts are secured to tissues using surgical sutures; this is both time consuming and carries the risk of adverse tissue response against the suturing material as well as sub-optimal contact between the tissue and the graft, The space that is formed between the graft and the tissue can become filled with liquid to form a seroma, which impairs the wound healing process. In addition, tight contact between graft and tissue is necessary for cellular ingrowth from the tissue towards the graft and vice versa. A biocompatible tissue adhesive will shorten the time required to secure the graft to its place using sutures, and at the same time will avoid adverse tissue response as well as increase the contact area between the graft and the target tissue and as a result reduce the risk of seroma and facilitate uniform cellular ingrowth and wound healing.

In ophthalmology, using a biocompatible tissue adhesive may be advantageous for glaucoma drainage device (GDD) implantation. Suture material is typically used for securing the plate to the sclera. Depending on the suture material used, the postoperative course can be marked by considerable discomfort caused by the conjunctival suture material. Additionally, absorbable suture material can induce inflammation, with localized surface and subconjunctival fibrosis creating an uneven conjunctival surface and excessive scarring. Non-absorbable sutures can erode through tissue postoperatively. Suturing the conjunctiva can compromise tissue that may be necessary for coverage or can cause complications such as buttonholes and tears. In addition, suturing the conjunctiva can sometimes be the most, time-intensive portion of the surgery (Kahook, M. Y., & Noecker, R. J.).

Another example where a biocompatible tissue adhesive may be required is the reinforcement of a herniation. In the repair of a hernia, a surgical mesh of appropriate size and shape is placed over the hernia and is secured in place using any suitable connecting means. Methods of mesh fixation that are commonly employed are placement of metal fixation devices (tacks) combined with either absorbable or non-absorbable transabdominal sutures and the insertion of two circles of tacks without the use of sutures (the double-crown technique). The fixation of mesh to the abdominal wall using tacks or stitches is recognized as a casual factor in postoperative pain by causing direct nerve and tissue injury and it has been found that patients undergoing laparoscopic ventral and incisional hernia repair tend to have more pain in the early postoperative period than after any other minimally invasive surgery (Wassenaar, E., et al).

In cardiology, the inability to obtain or maintain a secure seal between a vessel wall and a transluminally implanted intra-aneurysmal graft is a complication unique to the evolving technique of endovascular aneurysm exclusion (White, Yu, May, Chaufour, & Stephen, 1997). Surface fixation of the graft to the internal lumen, can help to prevent such complications.

In neurosurgery, there is frequently a need for dural grafts to cover defects resulting from retraction, shrinkage, or excision following neurosurgical procedures. Many substances have been tried as possible dural substitution, and different tissues and materials have been evaluated for use in dural repair, such as collagen membranes etc. however, the fixation of these membranes require suturing, which may be impractical in some cases. Thus, the need for non-penetrating fixation and sealing methods of such defect closure materials is increasing (Miscusi et al., 2014).

There is a medical need to use a biocompatible adhesive that is non-toxic, non-inflammatory and biodegradable.

SUMMARY OF THE INVENTION

The background art does not suggest a solution to secure implantable medical devices, based on biocompatible materials that are non-toxic, non-inflammatory and biodegradable.

The present invention overcomes these deficiencies of the background art by providing biocompatible materials for securing such implantable medical devices, for example by using an adhesive patch. Other forms of the securing device may be provided as described herein, for example as any suitable discrete adhesive unit.

The present invention, in at least some embodiments, provides a discrete adhesive unit for securing an implantable medical device to a tissue, comprising an adhesive layer and a non-adhesive layer, said adhesive layer comprising a biocompatible material, wherein said biocompatible material comprises a cross-linkable protein or polypeptide and one or more cross-linking materials, wherein said adhesive layer adheres said implantable medical device to the tissue. The unit may be in the form of an adhesive patch. Preferably, the non-adhesive layer comprises a reinforcing backing layer, wherein said reinforcing backing layer comprises at least one water erodible, film-forming polymer.

Optionally the non-adhesive layer is removable. Optionally and alternatively, the non-adhesive layer remains after adhering said implantable medical device to the tissue.

Optionally the adhesive layer wraps around at least a portion of the implantable medical device.

Optionally the unit is separately attached to at least a portion of the implantable medical device, separate from said adhesive layer.

The securing adhesive could be used for a wide variety of fields, including but not limited to ophthalmology, tissue grafts, cardiology, neurosurgery orthopedics, etc.

The present invention provides a composition of adhesive comprising a cross-linkable protein or polypeptide and one or more cross-linking materials according to at least some embodiments.

Preferably the biocompatible materials feature an enzymatically crosslinked gelatin matrix for securing a foreign body or an external device to a tissue. Cross-linking gelatin takes advantage of the adhesive properties of gelatin, by stabilizing the gelatin matrix and rendering it thermally stable in body temperature.

The cross-linkable protein or polypeptide may optionally comprise gelatin which may optionally be foamed, for example, by mixing the gelatin solution with pressurized air and/or other gas prior to drying. In some embodiments, the gelatin foam may be in a density range of 5 to 100 mg/cm$^3$ and preferably in the range of 10 to 50 mg/cm$^3$.

Optionally said foamed gelatin comprises dried or lyophilized foamed gelatin solution.

Optionally said gelatin is foamed gelatin. Optionally prior to foaming, the concentration of the gelatin solution is between 0.1% and 30% w/w. Optionally prior to foaming, the concentration of the gelatin solution is between 1% and 20% w/w. Optionally prior to foaming, the concentration of the gelatin solution is between 5% and 15% w/w.

Optionally said cross-linkable protein is present in a protein matrix, wherein said matrix has a density in a range of from 5 to 100 mg/cm$^3$. Optionally said density is in a range of from 10 to 50 mg/cm3.

Optionally said foamed gelatin is produced according to a method selected from the group consisting of a batch mixing process, a continuous mixing process, a chemical foaming process, or a Venturi foaming process.

Optionally said protein comprises gelatin and the cross-linking agent, such as an enzyme, comprises transglutaminase (TG). More preferably said transglutaminase comprises microbial transglutaminase.

Optionally the gelatin is incorporated into a gelatin matrix with said transglutaminase such that one or more of the following occur: a majority of enzyme activity is preserved throughout a process of preparation; enzyme is equally distributed across the gelatin matrix surface; and/or enzyme is embedded into the depth of the gelatin matrix (gradient or equal distribution). Optionally said transglutaminase is incorporated into said gelatin matrix according to one or more of mixing before drying said matrix or after drying said matrix, optionally wherein said matrix is dried to comprise no more than 10% moisture content. Optionally transglutaminase is present at a concentration of from 0.0006 to 2 mg transglutaminase/cm$^3$ gelatin matrix.

Optionally the tissue adhesive is in the form of a patch or other discrete unit for application. Such a discrete unit for application preferably further comprises a reinforcing backing layer which is non-adhesive and which can further include at least one water erodible, film-forming polymer (such as HPMC). The device backing may be composed of any polymeric material, of natural, semi-synthetic or synthetic nature, that is soluble in water to some extent such as polysaccharides, proteins etc.

The backing is required for the short duration in which there is a risk of the device coating sticking to unwanted surfaces or tissues, for example during handling of the device or during the surgery. Once the device has been placed and secured at the desired location the backing is no longer required, and therefore was designed to dissolve quickly.

The backing can be made of cellulose ether derivatives, such as HPMC (hydroxypropyl methylcellulose) or HPC (hydroxypropyl cellulose), HEC (hydroxyethyl cellulose) or EC (ethyl cellulose). The backing can be also made from crosslinked gelatin (enzymatic, physical or chemical cross-linking).

As used herein, "about" means plus or minus approximately ten percent of the indicated value.

Other features and advantages of the various embodiments of the invention will be apparent from the following detailed description, and from the claims.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the drawings.

DESCRIPTION OF PREFERRED EMBODIMENTS

The present invention is of compositions comprising a cross-linkable protein or polypeptide, and an agent which induces cross-linking of the cross-linkable protein, which are suitable for attaching a medical device to tissue.

According to preferred embodiments of the present invention, there is provided a composition for tissue adhesive in which the cross-linking material comprises transglutaminase and the cross-linkable protein comprises gelatin, in an attachment form that is suitable for attaching a medical device to tissue. For example, the attachment form may comprise a discrete unit, such as a patch for example. The cross-linked gelatin may form a matrix for example, which in turn may comprise an adhesive layer of the discrete unit. Optionally and preferably, the discrete unit also comprises a non-adhesive layer, such as a backing layer for example.

Suitable gelatin and transglutaminase can be obtained by any of the methods known and available to those skilled in the art. Gelatin may optionally comprise any type of gelatin which comprises protein that is known in the art, preferably including but not limited to gelatin obtained by partial hydrolysis of animal tissue and/or collagen obtained from animal tissue, including but not limited to animal skin, connective tissue (including but not limited to ligaments, cartilage and the like), antlers or horns and the like, and/or bones, and/or fish scales and/or bones or other components; and/or a recombinant gelatin produced using bacterial, yeast, animal, insect, or plant systems or any type of cell culture.

According to preferred embodiments of the present invention, gelatin from animal origins preferably comprises gelatin from mammalian origins and more preferably comprises one or more of pork skins, pork and cattle bones, or split cattle hides, or any other pig or bovine source. More preferably, such gelatin comprises porcine gelatin since it has a lower rate of anaphylaxis. Gelatin from animal origins may optionally be of type A (Acid Treated) or of type B (Alkaline Treated), though it is preferably type A.

Preferably, gelatin from animal origins comprises gelatin obtained during the first extraction, which is generally performed at lower temperatures (50-60° C., although this exact temperature range is an optional limitation).

The transglutaminase may optionally comprise any plant, animal, or microbe derived transglutaminase. Preferably the transglutaminase derived from *Streptoverticillium mobaraensis* is used.

The transglutaminase may optionally be in a composition comprising at least one other substance, such as a stabilizer or filler for example. Non-limiting examples of such materials include maltodextrin, hydrolyzed skim milk protein or any other protein substance, sodium chloride, safflower oil, trisodium phosphate, sodium caseinate or lactose, or a combination thereof preferably other than blood derived Factor XIII.

Although the optimal pH for activity of crude transglutaminase is 6.0, it also functions with high activity in the range of pH 5.0 to pH 8.0. Therefore, a composition according to the present invention for implant fixation preferably has a pH value in a range of from about 5 to about 8.

EXAMPLES

Example 1

Figure 1:
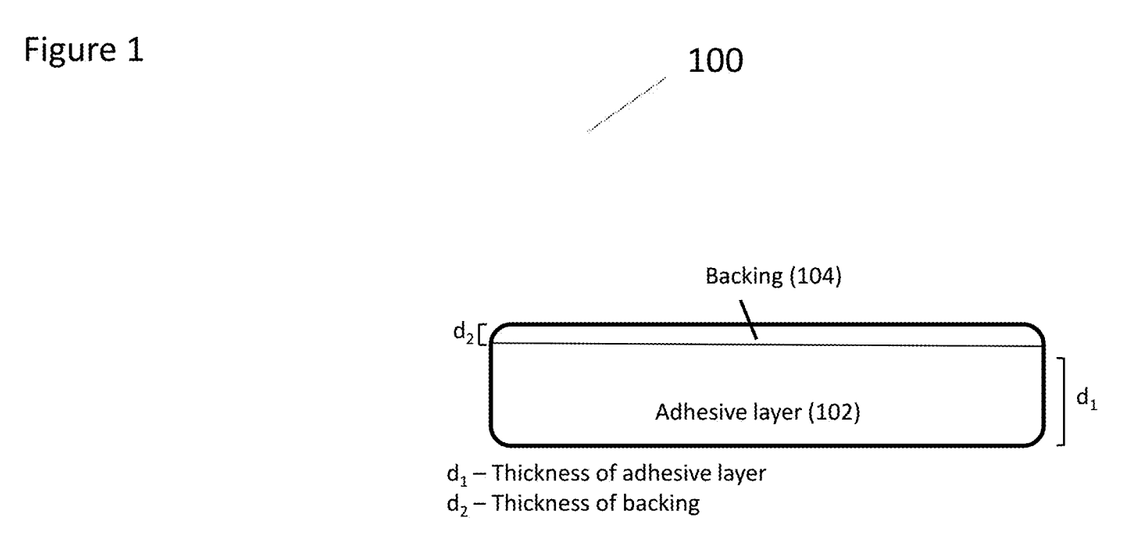
FIG. 1 represents a side schematic view of a non-limiting, exemplary, illustrative implementation of the adhesive material provided as a discrete unit.

Various exemplary implementations of the structure featuring the tissue adhesive composition are possible and are considered to fall within the present invention. FIG. 1 represents a side schematic view of a non-limiting, exemplary, illustrative implementation of the adhesive material provided as a discrete unit, in this case a patch 100, showing view of the layers. In this non-limiting example, two layers are provided, an adhesive layer 102 and a backing 104. As previously noted, backing 104 preferably is temporarily used in order for adhesive layer 102 (or layers) to be applied to both the tissue and to the implantable device (not shown). Such temporary use prevents having adhesive layer 102 (or layers) inadvertently adhere to an undesirable surface that is not the intended tissue and/or implantable device. Alternatively, the backing 104 or other non-adhesive layer remains after the implantable medical device is adhered to the tissue.

Each layer has a thickness d. In this non-limiting example, adhesive layer 102 has a thickness d1, which is optionally from 0.6 cm to 2 cm. Backing 104 has a thickness d2, which is optionally from 50 µm to 1000 µm.

Example 2

Figure 2A:
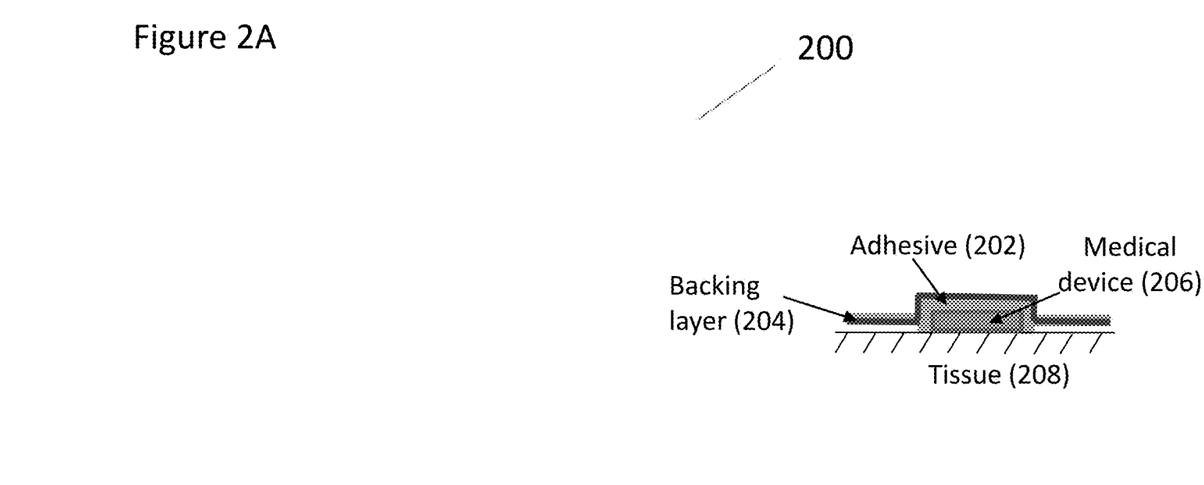
FIGS. 2A and 2B show non-limiting, exemplary embodiment of an adhesive material, provided as a discrete unit, with various placements in relation to the tissue and the implantable device.

The adhesive can be used in various ways. FIGS. 2A and 2B show non-limiting, exemplary embodiments of an adhesive material, provided as a discrete unit, with various placements in relation to the tissue and the implantable device. In the configuration shown in FIG. 2A, an adhesive material 200 features an adhesive layer 202 and a backing 204. Adhesive layer 202 is placed to adhere to an implantable device 206 which in turn is placed against the tissue 208. Adhesive layer 202 then wraps over and around at least a portion of implantable device 206 as shown, so as to contact tissue 208 that surrounds implantable device 206. The contact points at tissue 208 that surrounds implantable device 206 act to fixate adhesive layer 202 to tissue 208, while the contact points to implantable device 206 act to fixate adhesive layer 202 to implantable device 206. Backing 204 is non-adhesive and may be removed after place of adhesive layer 202 and implantable device 206, or may alternatively remain, to avoid attachment of any other undesirable surface to adhesive layer 202.

Figure 2B:
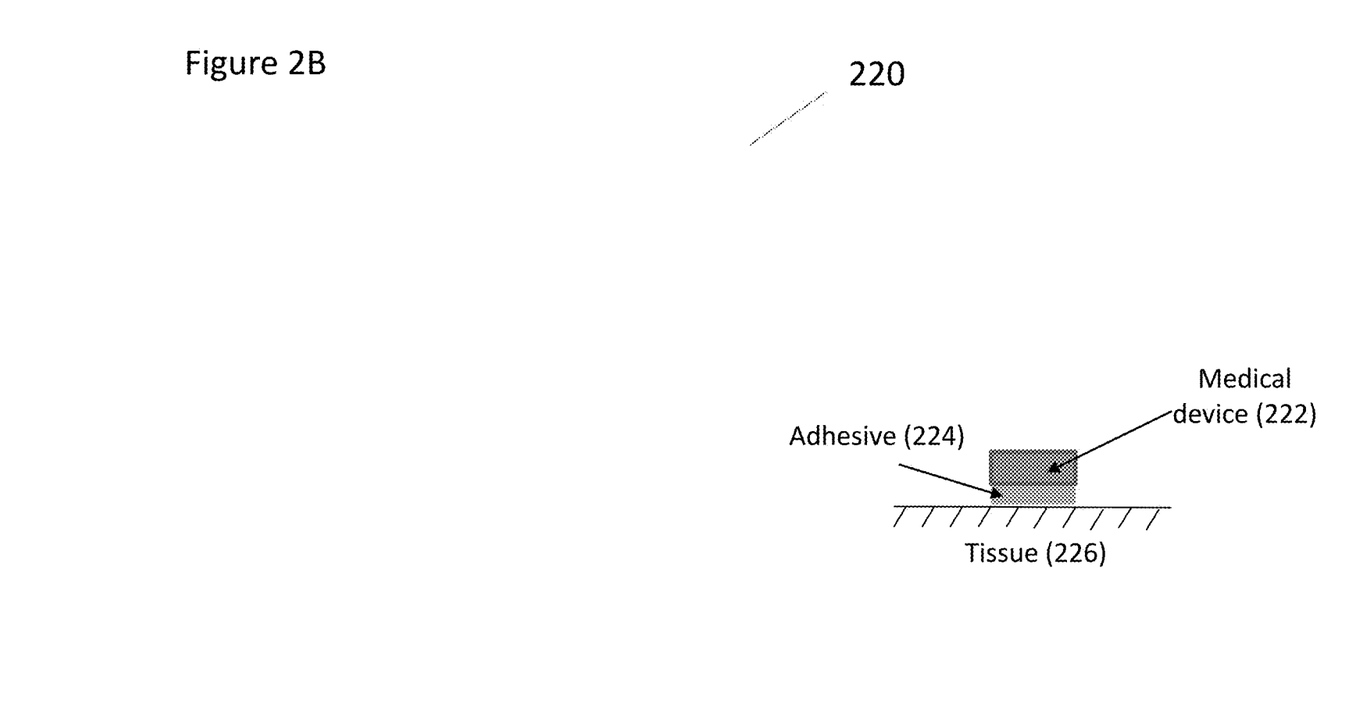

In the configuration shown in FIG. 2B, an adhesive material 220 features an adhesive layer 224. An implantable device 222 is adhered to a tissue 226, by placing adhesive layer 224 against tissue 226 and then placing implantable device 222 on adhesive layer 224. In this non-limiting example, optionally a backing is not provided, because the adhering surfaces of adhesive layer 224 are at least partially covered by contact with tissue 226 and implantable device 222.

Example 3

Various non-limiting examples of implementations of the adhesive material as a patch or other discrete unit are possible. For example, the adhesive can be a gelatin-based dry patch prepared from a 16% gelatin and 80 U/g_gelatin mTG solution. The solution is foamed at low pH (~3.8) in order to inhibit the enzymatic crosslinking, and dried by lyophilisation. The crosslinking is activated by wetting the patch when the latter is in contact with the muscle. Above it, a medical device is added. It can be, for example, a collagen scaffold (such as for example Ossix® Volumax, a thick dental regeneration product).

Figure 3:
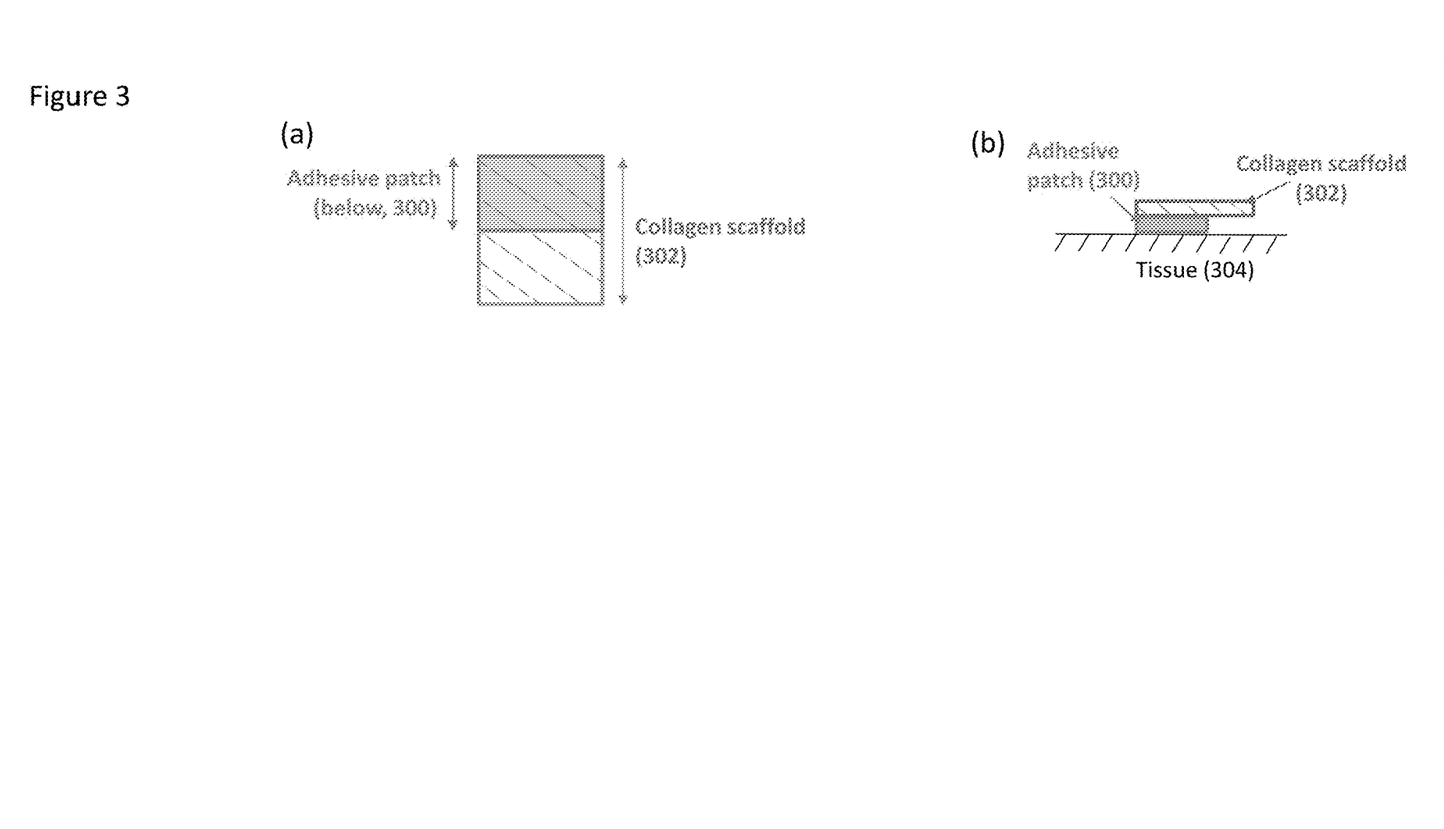
FIGS. 3A and 3B show schematic diagrams of a non-limiting example: of an adhesive patch, adhering to an implantable device such as a collagen scaffold for example.

FIGS. 3A and 3B show schematic diagrams of a non-limiting example of an adhesive patch which may be implemented according to the above description, adhering to an implantable device such as a collagen scaffold for example. FIG. 3A shows the top view and FIG. 3B shows the side view.

As shown, an adhesive patch 300 is provided which may be implemented as described with regard to FIG. 2B for example. Adhesive patch 300 is attached to a tissue 304, such as muscle for example. An implantable device 302 is then attached to adhesive patch 300, which in this non-limiting example is a collagen scaffold, such as the previously described Volumax product.

Optionally and alternatively the discrete unit, such as the adhesive patch, is separately attached to at least a portion of the implantable medical device, separate from the adhesive layer (not shown).

As another non-limiting example, the adhesive can be implemented as a gelatin-based dry patch prepared from a 2.5% gelatin and 80 U/g_gelatin mTG solution. The solution is foamed at low pH (~3.8) in order to inhibit the enzymatic crosslinking, and dried by lyophilisation. It can be used in order to secure a surgical mesh on a muscle to prevent or repair a hernia.

Example 4

In this non-limiting Example, the adhesive was implemented as a gelatin-based. dry patch prepared from a 16% gelatin and 80 U/g_gelatin mTG solution. The solution was foamed at low pH (~3.8) in order to inhibit the enzymatic crosslinking, and dried by lyophilisation. The crosslinking was activated by wetting the patch when the latter is in contact with the muscle. Above it, a collagen scaffold (such as for example Ossix® Volumax) was attached to the patch.

The following procedure was performed with a patch and implantable device that were configured as shown in FIGS. 3A and 3B:

Porcine abdominal wall tissue was heated to around 37° C. using a UV lamp. The temperature was checked using a non-contact IR (infrared) thermometer.

The dry patch was applied on the tissue of the muscle and immediately after the collagen scaffold was added above.

The muscle was covered with a wet gauze and then was placed at 37° C. in an air-incubator for 4 minutes, and then the adhesive strength was qualitatively tested.

Figure 4:
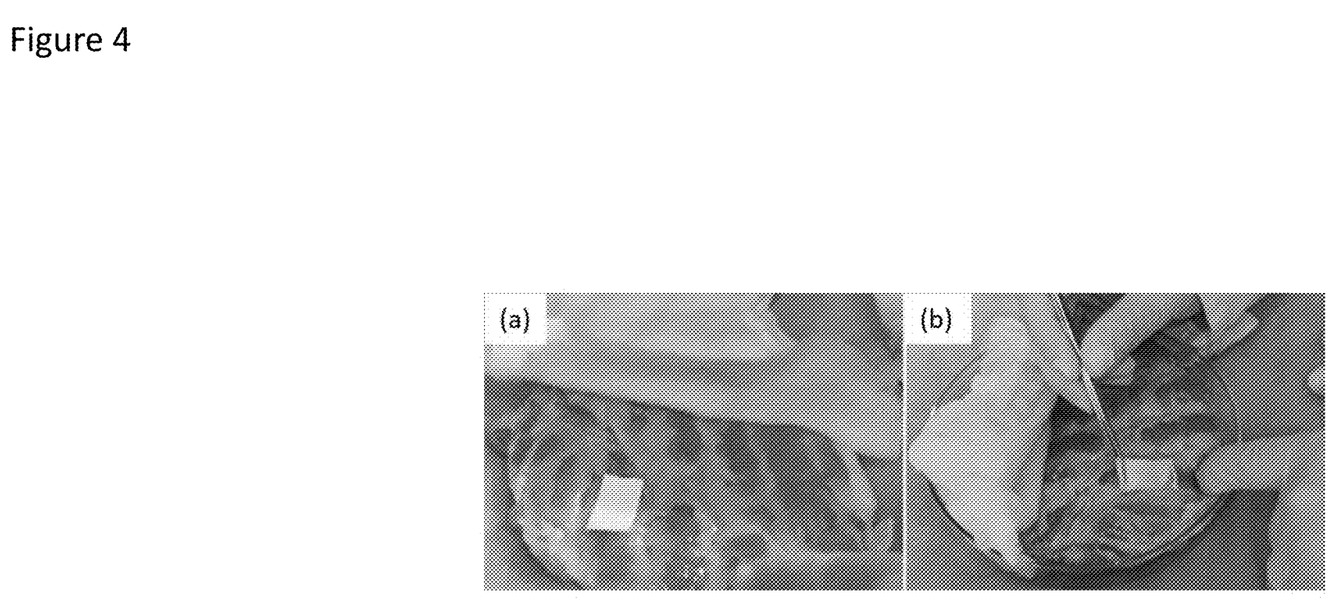
FIG. 4: Adhesion of a collagen scaffold using a gelatin-based dry patch on a pork abdominal muscle at: (a) time 0 and (b) after 4 minutes.

After 4 minutes, it was found that the collagen scaffold was well secured on the abdominal muscle, as shown with regard to FIG. 4.

Example 5

Figure 5:
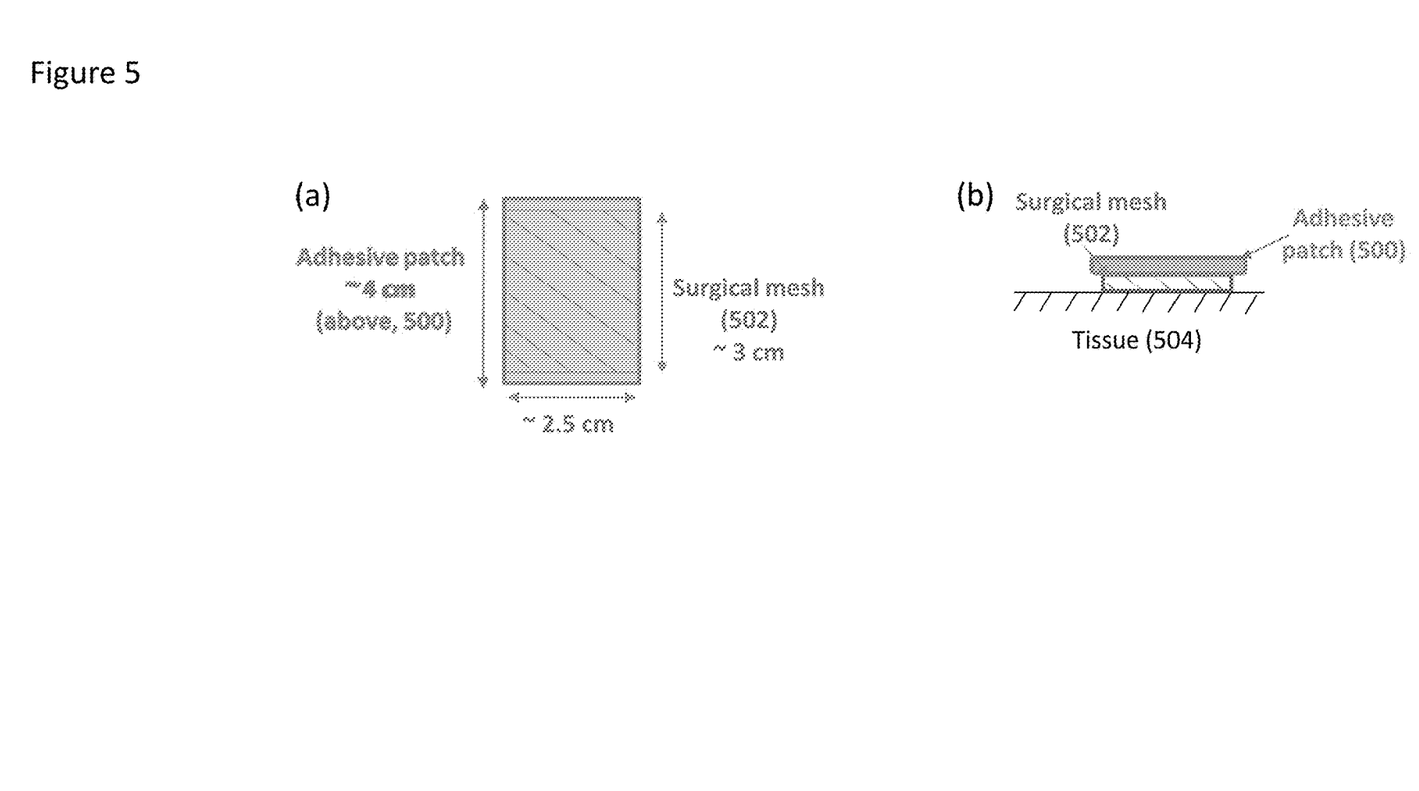
FIG. 5: Schematic representing the fixation of a surgical mesh using an adhesive dry patch: (a) top view; (b) side view.

FIGS. 5A and 5B show schematic diagrams of a non-limiting example of an adhesive patch which may be implemented according to the above description, adhering to an implantable device such as a surgical mesh for example. FIG. 5A shows the top view and FIG. 5B shows the side view.

As shown, an adhesive patch 500 is provided which may be implemented as described with regard to FIG. 2A for example. Adhesive patch 500 optionally is of a surface area from 2-600 cm$^2$, optionally in any suitable shape, including but not limited to square, rectangle, circle, oval and the like. Adhesive patch 500 is attached to an implantable device 502, which in turn is attached to a tissue 504, such as muscle for example. Implantable device 502 in this non-limiting example is a surgical mesh.

In this non-limiting Example, the adhesive was implemented as a gelatin-based dry patch prepared from a 2.5% gelatin and 80 U/g_gelatin mTG solution. The solution was foamed at low pH (~3.8) in order to inhibit the enzymatic crosslinking, and dried by lyophilisation. In this example, the adhesive patch was used in order to secure a surgical mesh on a muscle, for example to prevent or repair hernia.

The following procedure was performed with a patch and implantable device that were configured as shown in FIGS. 5A and 5B:

The muscle was heated to around 37° C. using a UV lamp. The temperature was checked using a non-contact IR thermometer.

The surgical mesh was placed on a porcine abdominal muscle and the dry patch was added above it to fixate it to the target tissue.

The muscle was covered with a wet gauze and then was placed at 37° C. in an air-incubator for 4 minutes, afterward the adhesive strength was quantitatively measured using a force gage instrument in a lap shear test.

Figure 6:
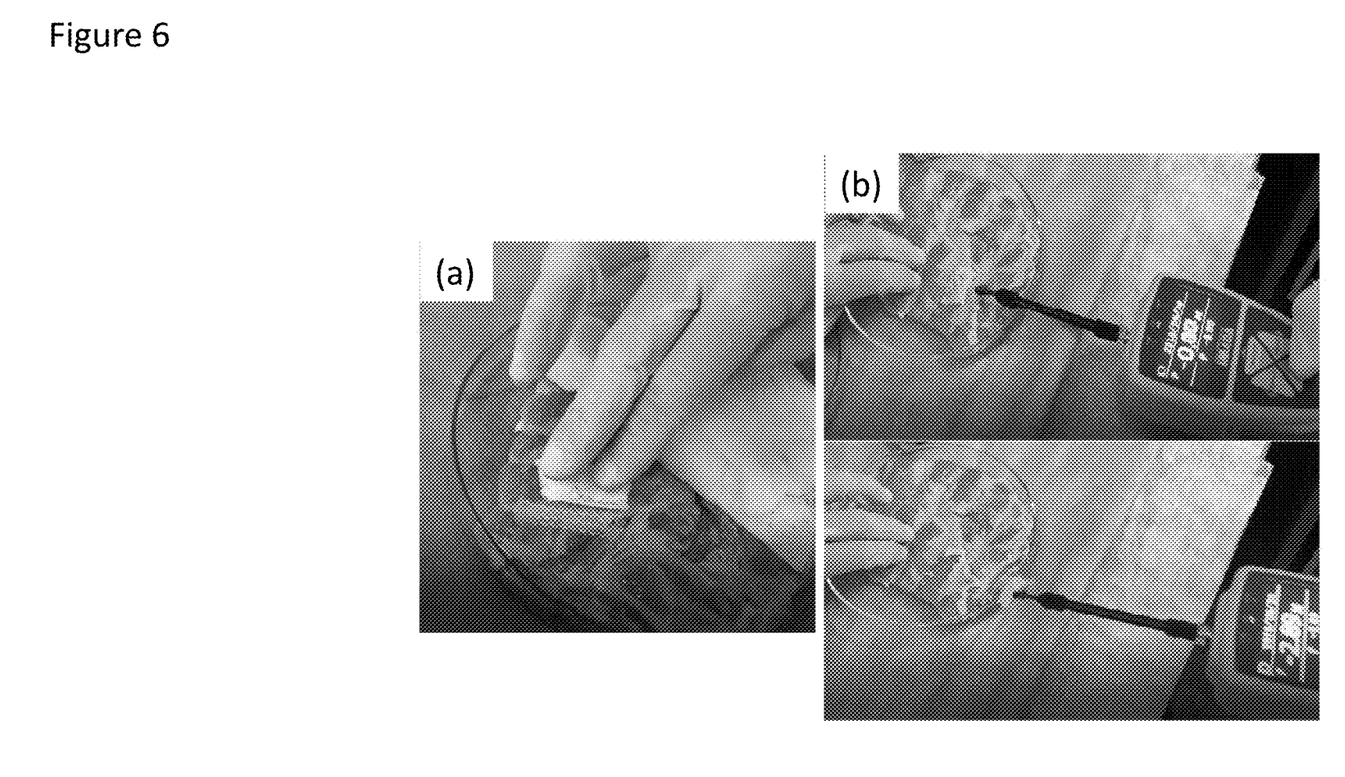
FIG. 6: Securing a surgical mesh using a gelatin-based dry patch on a porcine abdominal muscle, (a) at time 0, (b) after 4 minutes.

After 4 minutes at 37° C., it was found that the surgical mesh was well attached to the muscle. The adhesive strength measured using the gage force instrument was: 2.89 N=1.16 N/cm. The results are shown in FIG. 6.

REFERENCES

[1] Glickman M, Gheissari A, Money S, Martin J, Ballard J. Arch Surg 2002. 137, 326-31; discussion 332. Pursifull N F, Morey A F. Curr Opin Urol 2007, 17: 396-401.

[2] Tissue Adhesives in Clinical Medicine; 2nd ed.; Quinn, J. V., Ed.; B C Decker: Hamilton, Ontario Canada, 2005. Tissue Glue in Cosmetic Surgery; Saltz, R.; Toriumi, D. M., Eds. Quality Medical Publishing, Inc.: St. Louis, Mo., USA 2004.

[3] Kahook, M. Y., & Noecker, R. J. (2006). Fibrin glue-assisted glaucoma drainage device surgery. British journal of ophthalmology, 90(12), 1486-1489.

[4] Wassenaar, E., et al., Mesh-fixation method and pain and quality of life after laparoscopic ventral or incisional hernia repair: a randomized trial of three fixation techniques. Surgical endoscopy, 2010. 24(6): p. 1296-1302.

[5] Miscusi, M., Polli, F. M., Forcato, S., Coman, M. A., Ricciardi, L., Ramieri, A., & Raco, A. (2014). The use of surgical sealants in the repair of dural tears during non-instrumented spinal surgery. European Spine Journal, 23(8), 1761-1766. https://doi.org/10.1007/s00586-013-3138-1

[6] Reddy, M., Schöggl, A., Reddy, B., Saringer, W., Weigel, G., & Matula, C. (2002). A clinical study of a fibrinogen-based collagen fleece for dural repair in neurosurgery. *Acta Neurochirurgica*, 144(3), 265-269. https://doi.org/10.1007/s007010200034

[7] White, G. H., Yu, W., May, J., Chaufour, X., & Stephen, M. S. (1997). Endoleak as a Complication of Endoluminal Grafting of Abdominal Aortic Aneurysms: Classification, Incidence, Diagnosis, and Management. *Journal of Endovascular Surgery*, 4(2), 152-168. https://doi.org/10.1583/1074-6218(1997)004<0152:EAACOE>2.0. CO;2

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An implantable medical device
having a patch affixed to only a portion of a surface of the implantable medical device but not covering an entirety of the surface of the implantable medical device, the patch able to secure the implantable medical device to a tissue,
wherein the patch comprises an adhesive layer positioned to adhere the implantable medical device to the tissue and a non-adhesive backing layer covering the adhesive layer,
wherein the adhesive layer comprises foamed and lyophilized biocompatible gelatin and transglutaminase.

2. The implantable medical device of claim 1, wherein said backing layer is a reinforcing backing layer, wherein said reinforcing backing layer comprises at least one water erodible, film-forming polymer.

3. The implantable medical device of claim 2, wherein said reinforcing backing layer comprises at least one of cellulose ether derivatives, such as HPMC (hydroxypropyl methylcellulose) or HPC (hydroxypropyl cellulose), HEC (hydroxyethyl cellulose), EC (ethyl cellulose) or crosslinked gelatin, or a combination thereof.

4. The implantable medical device of claim 1, wherein said backing layer has a thickness of from 50 mm to 1000 mm.

5. The implantable medical device of claim 1, wherein said backing layer is removable.

6. The implantable medical device of claim 1, wherein said backing layer remains after adhering said implantable medical device to the tissue.

7. The implantable medical device of claim 1, wherein the foamed and lyophilized biocompatible gelatin and transglutaminase has a density in the range of 5 to 100 mg/cm$^3$.

8. The implantable medical device of claim 7, wherein the density is in the range of 10 to 50 mg/cm$^3$.

9. The implantable medical device of claim 1, wherein the foamed and lyophilized biocompatible gelatin and transglutaminase is formed by foaming a gelatin solution, and wherein prior to foaming, a concentration of gelatin in the gelatin solution is between 0.1% and 30% w/w.

10. The implantable medical device of claim 9, wherein prior to foaming, the concentration of gelatin in the gelatin solution is between 1% and 20% w/w.

11. The implantable medical device of claim 10 wherein prior to foaming, the concentration of gelatin in the gelatin solution is between 5% and 15% w/w.

12. The implantable medical device of claim 1, wherein the gelatin is incorporated with said transglutaminase in the adhesive layer such that one or more of the following occur: a majority of transglutaminase activity is preserved throughout a process of preparation; transglutaminase is equally distributed across the adhesive layer surface; and/or transglutaminase is embedded into the depth of the adhesive layer (gradient or equal distribution).

13. The implantable medical device of claim 1, wherein said transglutaminase is incorporated into said adhesive layer according to one or more of mixing before drying said adhesive layer or after drying said adhesive layer.

14. The implantable medical device of claim 1, wherein said adhesive layer is dried to comprise no more than 10% moisture content.

15. The implantable medical device of claim 1, wherein said transglutaminase is present in the adhesive layer at a concentration of from 0.0006 to 2 mg transglutaminase/cm$^3$.

16. The implantable medical device of claim 1, wherein said adhesive layer has a thickness of from 0.6 cm to 2 cm.

17. The implantable medical device of claim 1, wherein said patch has a surface area from 2 cm$^2$ to 600 cm$^2$.

18. The implantable medical device of claim 17, wherein said patch is in a shape of a square, rectangle, circle, or oval.

19. The implantable medical device of claim 1, wherein said adhesive layer is configured and positioned to adhere said implantable medical device to the tissue at a plurality of contact points on a surface of the tissue.

20. The implantable medical device of claim 1, wherein the patch is attached by adhesion to the implantable medical device.

* * * * *

UNITED STATES PATENT AND TRADEMARK OFFICE
CERTIFICATE OF CORRECTION

| | | |
|---|---|---|
| PATENT NO. | : 11,998,654 B2 | Page 1 of 1 |
| APPLICATION NO. | : 16/508356 | |
| DATED | : June 4, 2024 | |
| INVENTOR(S) | : Gideon Sturlesi et al. | |

It is certified that error appears in the above-identified patent and that said Letters Patent is hereby corrected as shown below:

In the Specification

At Column 1, Line 7, the word "seeming" should read --securing--

Signed and Sealed this
Twenty-first Day of January, 2025

Coke Morgan Stewart
*Acting Director of the United States Patent and Trademark Office*